(12) United States Patent
Bartholomaeus et al.

(10) Patent No.: US 8,173,164 B2
(45) Date of Patent: *May 8, 2012

(54) ORAL ADMINISTRATION FORMS FOR ADMINISTERING A FIXED TRAMADOL AND DICLOFENAC COMBINATION

(75) Inventors: Johannes Bartholomaeus, Aachen (DE); Iris Ziegler, Rott-Roetgen (DE)

(73) Assignee: Gruenenthal GmbH, Aachen (DE)

( * ) Notice: Subject to any disclaimer, the term of this patent is extended or adjusted under 35 U.S.C. 154(b) by 744 days.

This patent is subject to a terminal disclaimer.

(21) Appl. No.: 10/665,552

(22) Filed: Sep. 22, 2003

(65) Prior Publication Data
US 2004/0115267 A1    Jun. 17, 2004

Related U.S. Application Data

(63) Continuation-in-part of application No. 10/016,130, filed on Dec. 17, 2001, now abandoned, which is a continuation of application No. PCT/EP00/05386, filed on Jun. 13, 2000.

(30) Foreign Application Priority Data

Jun. 17, 1999   (DE) ................ 199 27 689.7

(51) Int. Cl.
*A61K 9/14*   (2006.01)
*A61K 9/20*   (2006.01)
*A61K 9/48*   (2006.01)

(52) U.S. Cl. .......... 424/489; 424/451; 424/464
(58) Field of Classification Search .............. None
See application file for complete search history.

(56) References Cited

U.S. PATENT DOCUMENTS

| | | | | |
|---|---|---|---|---|
| 4,690,927 A | * | 9/1987 | Voss et al. ............... | 514/282 |
| 5,041,430 A | * | 8/1991 | Addicks et al. ............ | 514/161 |
| 5,516,803 A | * | 5/1996 | Raffa ....................... | 514/570 |
| 5,597,560 A | * | 1/1997 | Bergamini et al. ......... | 424/78.04 |
| 5,679,660 A | * | 10/1997 | Bodley et al. ............. | 514/58 |
| 6,077,533 A | * | 6/2000 | Oshlack et al. ............ | 424/461 |
| 6,228,863 B1 | | 5/2001 | Palermo et al. | |
| 6,294,195 B1 | | 9/2001 | Oshlack et al. | |
| 6,319,514 B1 | * | 11/2001 | On .......................... | 424/436 |
| 6,558,701 B2 | * | 5/2003 | Bartholomaeus et al. .... | 424/472 |

FOREIGN PATENT DOCUMENTS

| EP | 0546676 A1 | | 6/1993 |
|---|---|---|---|
| EP | 0546676 A1 | * | 6/1993 |

OTHER PUBLICATIONS

Mok et al. "Analgesic Effect of Tramadal and Diclofenac in Combined Use"; American Society of Clinical Pharmacology and Therapeutics; Feb. 1996, p. 132.*

* cited by examiner

*Primary Examiner* — Susan Tran
(74) *Attorney, Agent, or Firm* — Crowell & Moring LLP

(57) ABSTRACT

An oral administration unit containing the active substances Tramadol and Diclofenac and/or physiologically acceptable salts thereof, in which both active substances are contained in the same administration unit as two separately formulated subunits.

25 Claims, 4 Drawing Sheets

ORAL ADMINISTRATION FORMS FOR ADMINISTERING A FIXED TRAMADOL AND DICLOFENAC COMBINATION

CROSS REFERENCE TO RELATED APPLICATIONS

This application is a continuation of international patent application no. PCT/EP00/05386, filed Jun. 13, 2000, designating the United States of America, the entire disclosure of which is incorporated herein by reference. Priority is claimed based on Federal Republic of Germany patent application no. DE 199 27 689.7, filed Jun. 17, 1999.

BACKGROUND OF THE INVENTION

The present invention relates to an oral administration unit containing the active substances Tramadol and Diclofenac and/or their respective physiologically compatible salts, the two active substances being present in subunits separately formulated in each case, in the same administration unit.

Tramadol is an analgesic used to treat severe and moderately severe pain, whose mode of action is not based on a pure opioid mechanism. Tramadol also does not exhibit the characteristic side effects of an opioid. In some cases nausea is observed as an undesirable accompanying symptom.

Other known, non-opioid analgesics suitable for treating less severe pain include steroid-free analgesics such as Diclofenac-Na, acetylsalicylic acid or Ibuprofen.

Furthermore, for the treatment of moderate to severe pain it is recommended by the WHO to combine opioid analgesics with non-steroidal analgesics in order to produce a more effective pain relief and possibly reduce the necessary administration amounts.

European Patent EP-B-0 546 676 discloses for example that the combination of Tramadol-HCl with non-steroidal anti-inflammatories, such as for example Ibuprofen, in a composition ratio of 1:1 to 1:200 produces a synergistically enhanced analgesic action. Tramadol-HCl and Diclofenac-Na form a sparingly soluble compound however. It is therefore to be expected that the bioavailability of the two active substances is reduced and higher dosages are required in order to compensate for this.

SUMMARY OF THE INVENTION

It is an object of the invention to provide a new pharmaceutical dosage form for combined administration of Tramadol and Diclofenac.

Another object of the invention is to combine the two active substances Tramadol and Diclofenac and/or their respective physiologically compatible salts in a common administration unit without impairing the release profiles of the two active substances or reducing their bioavailability.

These and other objects of the invention are achieved in accordance with the present invention by providing an oral administration unit that contains the two active substances Tramadol and Diclofenac and/or their respective physiologically compatible salts, with the two active substances, respectively, contained in separately formulated subunits in the same administration unit.

Preferably the subunits contain as physiologically compatible salts of Tramadol: Tramadol hydrochloride, Tramadol hydrobromide, Tramadol sulfate, Tramadol phosphate, Tramadol fumarate, Tramadol succinate, Tramadol maleate, Tramadol nitrate, Tramadol acetate, Tramadol propionate, Tramadol malonate, Tramadol citrate, Tramadol tartrate, Tramadol benzoate, Tramadol salicylate, Tramadol phthalate and/or Tramadol nicotinate. Particularly preferably the subunits contain Tramadol hydrochloride. Preferably the subunits contain as physiologically compatible salts of Diclofenac: Diclofenac-sodium, Diclofenac-potassium, Diclofenac-calcium, Diclofenac-magnesium and/or Diclofenac-cholestyramine. Particularly preferably the subunits contain Diclofenac-sodium.

Preferably the oral administration unit contains the active substances Tramadol and Diclofenac in a quantitative ratio of $\leqq 1:4$ to $4:\leqq 1$, preferably 1:4 to 4:1, particularly preferably in a quantitative ratio of 1:2 to 3:1, and most particularly preferably in a quantitative ratio of 1:1 to 2.5:1.

The subunits within the context of the invention are solid medicament formulations which, in addition to the respective active substance and/or a respective physiologically compatible salt thereof, also contain conventional auxiliary substances and additives.

Preferably the subunits are present in multiparticulate form, such as for example as microtablets, microcapsules, ion-exchange resinates, granules, active substance crystals or pellets. Particularly preferably the subunits are present in the form of granules, active substance crystals or pellets. Most particularly preferably the form of the subunits comprises pellets or composite pellets produced by extrusion and/or spheronisation.

The oral administration unit may also contain at least one of the two active substances in a retarded (delayed release), optionally multiparticulate form, preferably both active substances in a retarded, optionally multiparticulate form.

The oral administration unit may also contain at least one of the active substances in a non-retarded form in addition to its retarded form. By combination with the immediately released active substance, a rapid pain relief can be achieved and the slow release from the retarded form permits the therapeutic blood level to be maintained over a prolonged period. Particularly preferably the release of the active substances is adjusted so that the oral administration unit has to be administered at most twice, and preferably only once per day. Persons skilled in the art will know from the action mechanism of the analgesics what mixing ratios of these active substances have to be used in order to achieve the desired effect.

The release profile of the oral administration units is preferably controlled so that with a twice-daily administration the Tramadol and Diclofenac are released in an amount of $\geqq 70$ wt. % and $\geqq 60$ wt. %, respectively, within 8 hours. The invention accordingly also provides oral administration units for a twice-daily administration, which are characterized in that the Tramadol and Diclofenac are released in an amount of $\geqq 70$ wt. % and $\geqq 60$ wt. % respectively within 8 hours.

In the case of once daily administration, the release profile is preferably controlled so that the Tramadol and Diclofenac are released in an amount of $\geqq 70$ wt. % and $\geqq 60$ wt. %, respectively, within 16 hours. The invention accordingly also provides oral administration units for a once daily administration, which are characterized in that the Tramadol and Diclofenac are released in an amount of $\geqq 70$ wt. % and $\geqq 60$ wt. %, respectively, within 16 hours.

With oral administration units that contain multiparticulate subunits with gastric juice-resistant coatings or which themselves comprise gastric juice-resistant coatings, the aforementioned release profiles as regards Tramadol as well as the residence time in the stomach have to be readjusted.

The delayed release of the respective active substances in the respective subunits may preferably be achieved by a retarding coating, binding to an ion-exchange resin, embedding in a retarding matrix, or a combination thereof.

The delayed release effect is preferably achieved by means of retarding coatings. Suitable retarding coatings comprise water-insoluble waxes or polymers, such as for example acrylic resins, preferably poly(meth)acrylates, or water-insoluble celluloses, preferably ethylcellulose. These materials are known from the prior art, for example Bauer, Lehmann, Osterwald, Rothgang "Überzogene Arzneiformen" ("Coated Medicament Forms") Wissenschaftliche Verlagsgesellschaft mbH Stuttgart, 1988, p. 69 ff. They are introduced here by way of reference.

In order to adjust the release rate of the active substance, in addition to the water-insoluble polymers the retard coatings may optionally also contain, preferably in amounts of up to 30 wt. %, non-retarding, preferably water-soluble, polymers such as polyvinylpyrrolidone or water-soluble celluloses, preferably hydroxypropylmethyl-cellulose or hydroxypropylcellulose, and/or hydrophilic pore-forming agents such as sucrose, sodium chloride or mannitol and/or the known plasticisers.

In addition the multiparticulate subunits may also contain further coatings. Additional coatings that may be present include those that dissolve depending on the pH value. In this way the subunits may pass undissolved through the stomach and be released only in the intestine. Coatings may also be used that serve to improve the taste.

A further conventional retardation procedure is to bind the active substances to ion-exchange resins. Cholestyramine is preferably used as anionic ion-exchange resin to retard the active substance Diclofenac. Polystyrene sulfonates are preferably used as cationic ion-exchange resin to retard the active substance Tramadol.

In order to achieve delayed release, the active substances may also be contained, preferably uniformly distributed, in a retarding matrix in the subunits. Suitable matrix materials which may be used include physiologically compatible, hydrophilic materials that are known to persons skilled in the art. Polymers, particularly preferably cellulose ethers, cellulose esters and/or acrylic resins, are preferably used as hydrophilic matrix materials. Ethylcellulose, hydroxymethylcellulose, hydroxypropylmethylcellulose, hydroxypropylcellulose, poly(meth)acrylic acid and/or their derivatives such as their salts, amides or esters may most particularly preferably be used as matrix materials.

Also preferred are matrix materials of hydrophobic materials such as hydrophobic polymers, waxes, fats, long-chain fatty acids, fatty alcohols or corresponding esters or ethers or their mixtures. Monoglycerides or diglycerides of $C_{12}$-$C_{30}$ fatty acids and/or $C_{12}$-$C_{30}$ fatty alcohols and/or waxes or their mixtures are particularly preferably used as hydrophobic materials.

It is also possible to use mixtures of the aforementioned hydrophilic and hydrophobic materials as a retarding matrix material.

The administration form of the oral administration unit according to the invention is preferably a sachet, a capsule or a tablet, particularly preferably a capsule or a tablet. Preferably the tablet is a pellet-type tablet that particularly preferably decomposes rapidly.

To this end the tablet may decompose on contact with aqueous media into the subunits and release the active substances in a spatially separated manner. As release agents that separate the subunits from one another on contact with aqueous media, there may be used starch, hydroxypropylcellulose having a low degree of substitution, Crospovidone and/or Croscarmelose.

Preferably the administration unit according to the invention in tablet form has at least one score mark that permits the dose to be subdivided, preferably halved. This enables the dose to be matched to the individual requirements of the patient, corresponding to the amount of the analgesics to be administered individually.

The multiparticulate subunits as well as the oral administration unit according to the invention may be produced by various methods known to persons skilled in the art. These methods are known from the prior art, and are described for example in "Pharmaceutical Pelletization Technology", Drugs and the Pharmaceutical Sciences Vol. 37, Verlag Marcel Dekker. They are introduced here by way of reference.

If the oral administration unit according to the invention, such as for example the tablet, contains coatings, then these may be applied by conventional processes, such as for example dragée coating, spraying of solutions, melts, dispersion or suspensions, by melt processes or by powder application processes.

These coatings may be retarding or non-retarding. Retarding coatings consist of the aforementioned materials. In addition to the retarding coating, the oral administration unit according to the invention may contain at least one further coating. Such a coating may dissolve in a pH-dependent manner for example. In this way the oral administration unit may pass undissolved through the stomach and be released only in the intestines. A further coating may also serve to improve the taste.

BRIEF DESCRIPTION OF THE DRAWINGS

The invention will be described in further detail hereinafter with reference to the accompanying drawings in which.

DETAILED DESCRIPTION OF EMBODIMENTS

Figure 1:
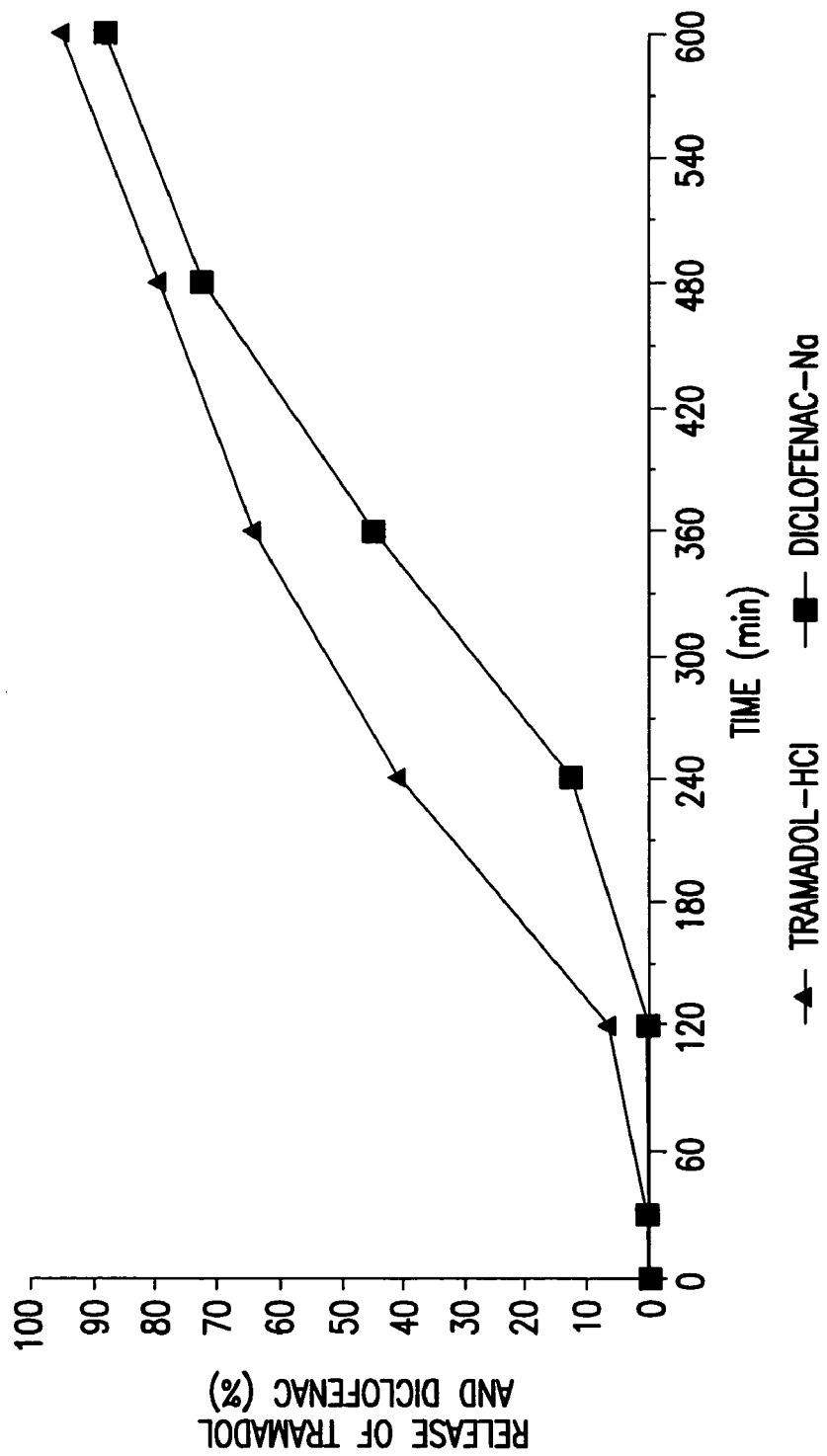
FIG. 1 is a graph of the release of Tramadol and Diclofenac from a first oral administration unit according to the invention.

The release profiles of the preparations according to the invention produced in accordance with the examples was determined as follows:

The preparations were added either to a rotating basket apparatus (Examples 1 and 3) or to an apparatus equipped with a blade stirrer (Examples 2 and 4) according to the European Pharmacopoeia at a temperature of 37° C. and a rotational speed of 100 $\min^{-1}$ (Examples 1 and 3) or 50 $\min^{-1}$ (Examples 2 and 4) for 2 hours in 600 ml of enzyme-free artificial gastric juice (pH 1.2). The preparations were then treated for a further 8 hours (Example 3, further 6 hours) in 900 ml of enzyme-free artificial intestinal juice (pH 7.2). This pH value was maintained up to the start of the investigation. The amount of the respective active substance, i.e. Tramadol or Diclofenac, released in each case at specified time intervals was determined by high performance liquid chromatography (HPLC). The illustrated values and curves are the respective mean values of six samples.

The following examples serve to illustrate the invention in further detail without however restricting the general inventive concept.

EXAMPLE 1

Tramadol pellets with an active substance content of 55 wt. % were produced by aqueous granulation with microcrystalline cellulose and hydroxypropylcellulose with a low degree of substitution, followed by extrusion/spheronisation. The pellets of size 800-1250 μm were dried and then coated in a fluidized bed at an inflow air temperature of 60° C., initially with 3 wt. % of hydroxypropylmethylcellulose and talcum as an undercoat, and then with 11 wt. % of Surelease E-7-7050 as a delayed release coating. The film application amounts are given in weight percent relative to the initial weight of the pellets or pellets plus the undercoat.

Diclofenac pellets with an active substance content of 37 wt. % were produced by aqueous granulation with microcrystalline cellulose and lactose monohydrate, followed by extrusion/spheronisation. The pellets of size 800-1250 μm were dried and then coated in a fluidized bed at an inflow air temperature of 60° C., initially with 1 wt. % of hydroxypropylmethylcellulose as an undercoat and then with 13 wt. % of Surelease E-7-7050 as a delayed release coating. The film application amounts are given in weight percent relative to the initial weight of the pellets or pellets plus undercoat. The Diclofenac retard pellets were then dried and heat-treated in a drying cabinet at 60° C. for 2 hours.

Hard gelatin capsules of size 0 were then filled with 160 mg of the aforedescribed Tramadol retard pellets (=75 mg of Tramadol-HCl) and 160 mg of the aforedescribed Diclofenac retard pellets (=50 mg Diclofenac-Na) in a suitable encapsulating machine. The resulting 75/50 mg Tramadol/Diclofenac delayed release capsules had the following composition:

| Composition | Per Capsule |
| --- | --- |
| Tramadol Retard Pellets (residual moisture:2.5%) | 160 mg |
| Tramadol-HCl | 75.0 mg |
| Microcrystalline cellulose (Avicel PH 105 from FMC) | 31.4 mg |
| Low substituted hydroxypropylcellulose (I-HPC LH 31 from ShinEtsu) | 30.0 mg |
| Opadry OY 29020 clear (Colorcon) | 2.9 mg |
| Talcum | 1.2 mg |
| Surelease E-7-7050 (Colorcon) | 15.5 mg |
| (Dry substance fraction) | mg |
| Diclofenac Retard Pellets (residual moisture:3.6%) | 160 mg |
| Diclofenac-Na | 50.0 mg |
| Microcrystalline cellulose (Avicel PH 105 from FMC) | 75.0 mg |
| Lactose · H$_2$O | 10.1 mg |
| Opadry OY 29020 clear (Colorcon) | 1.4 mg |
| Surelease E-7-7050 (Colorcon) | 17.8 mg |
| (Dry substance fraction) | mg |

The release profile was as shown in the following Table and is also illustrated in FIG. 1:

| | Released Fraction in % | |
| --- | --- | --- |
| Time in mins. | for Tramadol | for Diclofenac |
| 30 | 0.4 | 0.3 |
| 120 | 7 | 0.3 |
| 240 | 41 | 12 |
| 360 | 64 | 44 |
| 480 | 79 | 71 |
| 600 | 95 | 87 |

Figure 2:
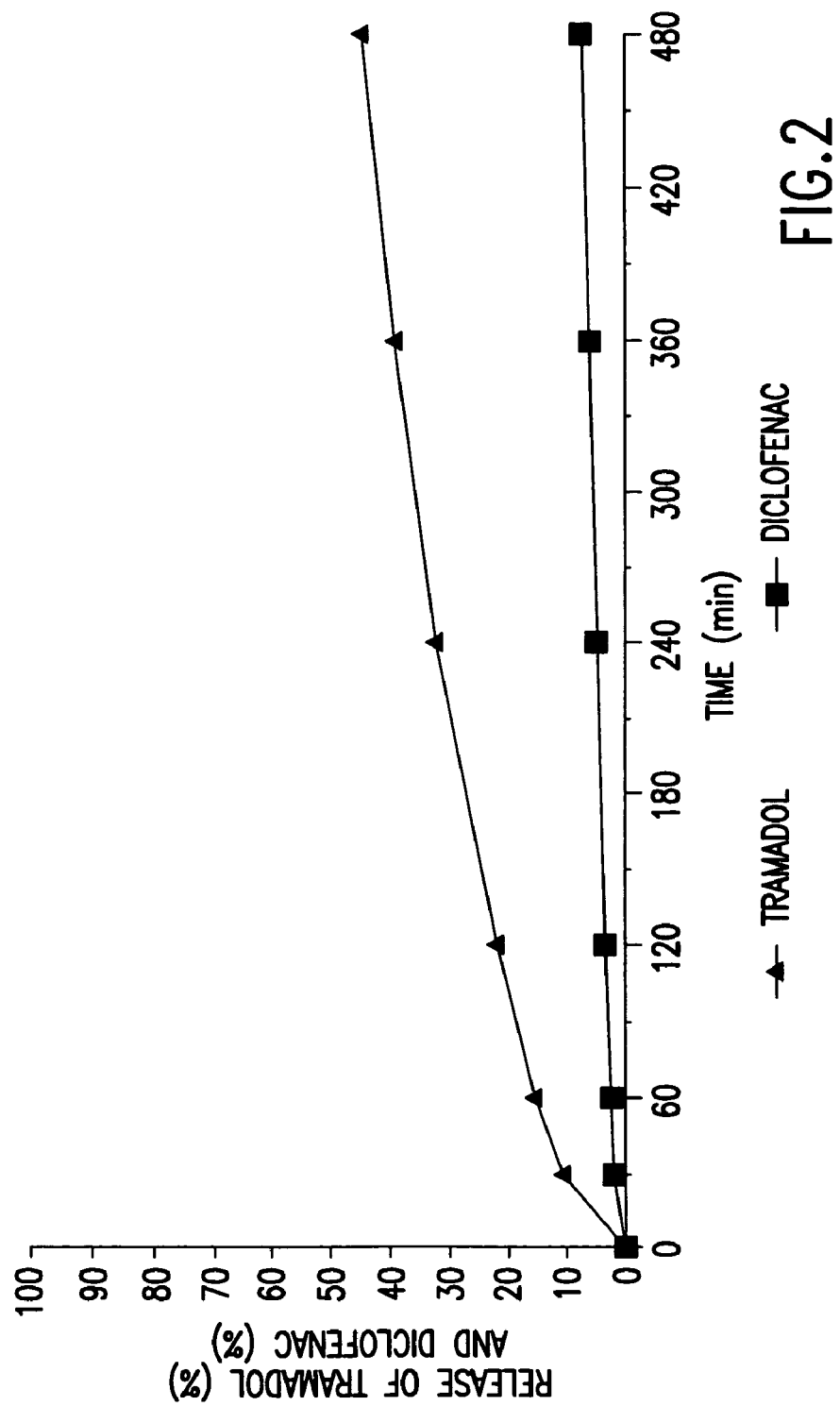
FIG. 2 is a graph of the release of Tramadol and Diclofenac from a second oral administration unit.

FIG. 2 shows the release profile of a matrix tablet of diameter 12 mm containing 75 mg of Tramadol-HCl and 50 mg of Diclofenac-Na compressed in a common hydrophilic matrix consisting of hydroxypropylmethylcellulose. A comparison of FIG. 1 with FIG. 2 shows that the released amount of the active substances Tramadol and Diclofenac from the oral administration unit according to the invention after 8 hours is significantly greater than the release from the so-called common matrix tablets.

Figure 3:
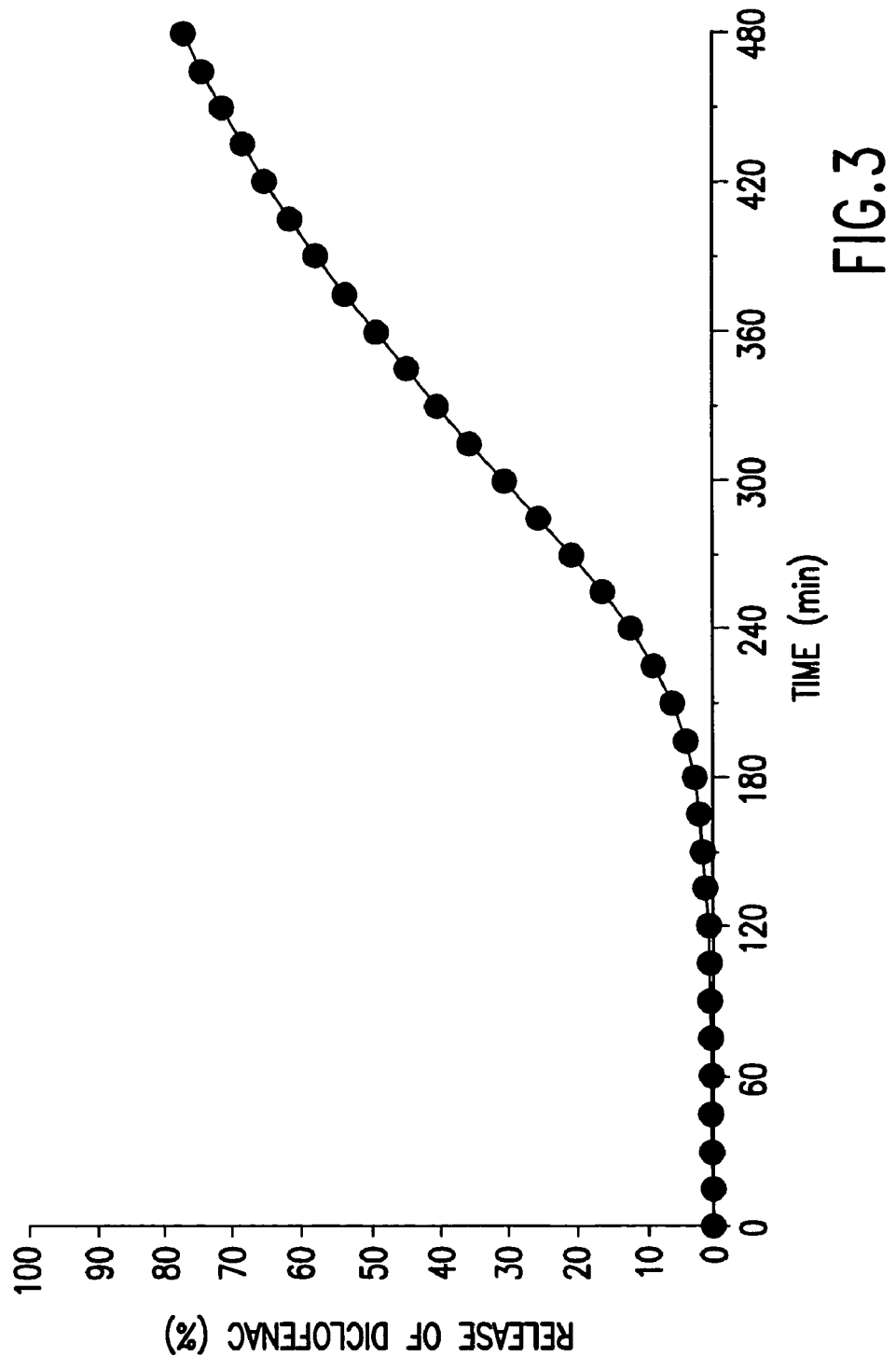
FIG. 3 is a graph of the release of Diclofenac from another oral administration unit.

FIG. 3 shows the release of Diclofenac from Diclofenac retard pellets that have been coated with a 1 wt. % undercoat of hydroxypropylmethylcellulose (Opadry OY 29020, similar to Example 1) and a 13 wt. % Surelease 7-7050 coat.

Figure 4:
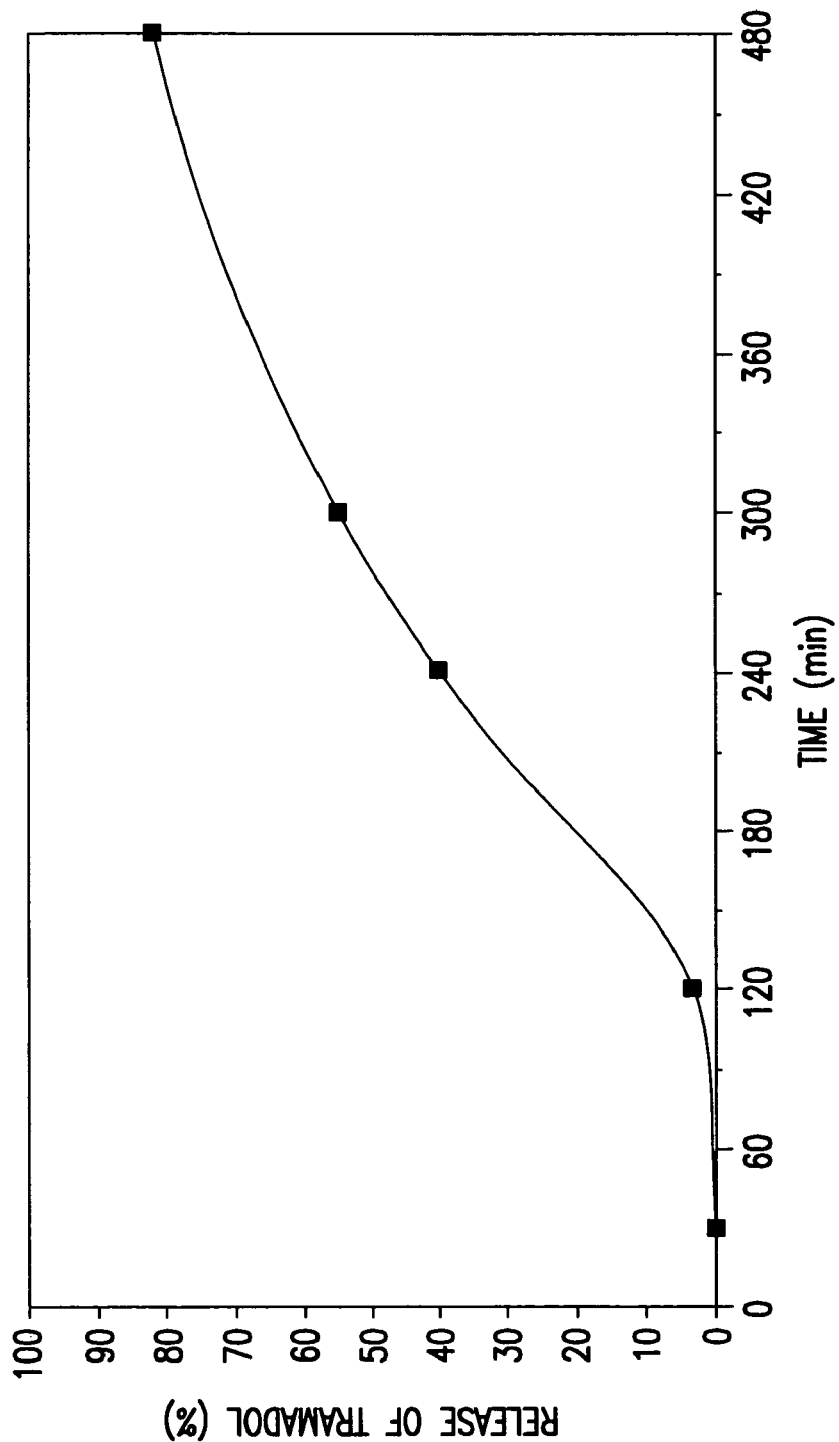
FIG. 4 is a graph of the release of Tramadol from another oral administration unit.

FIG. 4 shows the release of Tramadol from Tramadol retard pellets with a 3 wt. % undercoat of hydroxypropylmethylcellulose (Opadry OY 29020, similar to Example 1) and talcum, and an 11 wt. % Surelease 7-7050 coating.

A comparison of FIG. 1 with FIGS. 3 and 4 shows that the released amounts and the release profiles of Tramadol and Diclofenac from the oral administration units according to the invention correspond to the amounts and release profiles from the forms containing in each case only Tramadol or only Diclofenac.

EXAMPLE 2

Tramadol retard pellets and Diclofenac retard pellets were produced in a similar manner to Example 1. Tramadol initial dose pellets were produced in a similar manner to the delayed release Tramadol pellets, but were coated not with the Surelease E-7-7050 coating but simply with 3% of an undercoat consisting of Opadry OY 29020 clear and talcum. The three types of pellets were mixed with one another in a Bohle container mixer for 10 minutes.

368 mg of pellets, corresponding to a dose of 100 mg of Tramadol hydrochloride and 50 mg of Diclofenac-Na, were initially mixed with 30 mg of Crospovidon and then with 330.6 mg of Cellactose® and 7.4 mg of magnesium stearate and compressed into 7×14 mm size tablets weighing 736 mg and provided with a score mark. These composite pellets decompose again in an aqueous medium into the individual pellets.

| Composition | Per Tablet |
| --- | --- |
| Tramadol Retard Pellets (residual moisture:2.5%) | 160 mg |
| Tramadol-HCl | 75.0 mg |
| Microcrystalline cellulose (Avicel PH 105 from FMC) | 31.4 mg |
| Low substituted hydroxypropylcellulose (I-HPC LH 31 from ShinEtsu) | 30.0 mg |
| Opadry OY 29020 clear (Colorcon) | 2.9 mg |
| Talcum | 1.2 mg |
| Surelease E-7-7050 (Colorcon) | 15.5 mg |
| (Dry substance fraction) | |
| Tramadol Initial Dose Pellets (residual moisture:2.5%) | 48 mg |
| Tramadol-HCl | 25.0 mg |
| Microcrystalline cellulose (Avicel PH 105 from FMC) | 10.5 mg |
| Low substituted hydroxypropylcellulose (l-HPC LH 31 from ShinEtsu) | 10.0 mg |
| Opadry OY 29020 clear (Colorcon) | 0.9 mg |
| Talcum | 0.4 mg |
| Dicl fenac Retard Pellets (residual moisture: 3.6%) | 160 mg |
| Diclofenac-Na | 50.0 mg |
| Microcrystalline cellulose (Avicel PH 105 from FMC) | 75.0 mg |
| Lactose · H$_2$O | 10.1 mg |
| Opadry OY 29020 clear (Colorcon) | 1.4 mg |
| Surelease E-7-7050 (Colorcon) | 17.8 mg |
| (Dry substance fraction) | |
| Cellactose ® (Meggle) | 330.6 mg |
| Crospovidon (Kollidon CL from BASF) | 30 mg |
| Magnesium stearate | 7.4 mg |
| Total | 736 mg |

The release profile was as follows:

| Time in mins. | Released Fraction in % | |
|---|---|---|
| | for Tramadol | for Diclofenac |
| 30 | 28 | 0 |
| 120 | 35 | 0 |
| 240 | 62 | 20 |
| 360 | 78 | 40 |
| 480 | 89 | 78 |
| 600 | 100 | 98 |

EXAMPLE 3

Tramadol pellets with an active substance content of 55 wt. % were produced by aqueous granulation with microcrystalline cellulose and low substituted hydroxy-propylcellulose, following by extrusion/spheronisation. The pellets of size 800-1250 μm were dried and then coated in a fluidized bed at an inflow air temperature of 60° C. with 15 wt. % of retard coating relative to the initial weight of the pellets. The dried Tramadol retard pellets were then dried for a further 2 hours at 60° C. in a drying cabinet in order to adjust the release profile, before being coated with an overcoat of 0.6 wt. % of hydroxypropylmethylcellulose, relative to the initial weight of the pellets plus retard coating.

Diclofenac pellets with an active substance content of 37 wt. % were produced by aqueous granulation with microcrystalline cellulose and lactose monohydrate, followed by extrusion/spheronisation. The dried pellets of size 800-1250 μm were dried and then coated in a fluidized bed at 60° C. inflow air temperature with 16 wt. % of retard coating, relative to the initial weight of the pellets. The dried Diclofenac retard pellets were then heat-treated in a drying cabinet at 60° C. for 24 hours.

Hard gelatin capsules of size 0 were then filled with 216 mg of Tramadol retard pellets (=100 mg of Tramadol-HCl) and 162 mg of Diclofenac retard pellets (=50 mg Diclofenac-Na). The resulting capsules had the following composition:

| Composition | Capsule |
|---|---|
| Tramadol Retard Pellets (residual moisture:2.5%) | 216 mg |
| Tramadol-HCl | 100.0 mg |
| Microcrystalline cellulose (Avicel PH 105) | 42.0 mg |
| Low substituted hydroxypropylcellulose (I-HPC LH 31) | 40.0 mg |
| Aquacoat ECD 30 (dry substance fraction) | 18.6 mg |
| Dibutyl sebacate | 4.4 mg |
| Talcum | 4.3 mg |
| Tween 80 | 0.002 mg |
| Opadry OY 29020 clear | 1.3 mg |
| Diclofenac Retard Pellets (residual moisture:3.3%) | 162 mg |
| Diclofenac-Na | 50.0 mg |
| Microcrystalline cellulose (Avicel PH 105) | 75.0 mg |
| Lactose · H$_2$O | 10.1 mg |
| Aquacoat ECD 30 (dry substance fraction) | 14.0 mg |
| Opadry OY 29020 clear | 2.0 mg |
| Dibutyl sebacate | 3.0 mg |
| Talcum | 2.6 mg |
| Tween 80 | 0.002 mg |

The release profile was as follows:

| Time in mins. | Released Fraction in % | |
|---|---|---|
| | for Tramadol | for Diclofenac |
| 120 | 43 | 1 |
| 240 | 86 | 39 |
| 360 | 94 | 59 |
| 480 | 98 | 72 |

EXAMPLE 4

Tramadol hydrochloride and microcrystalline cellulose were granulated with an aqueous solution of Povidon K30, dried, screened, and after mixing with magnesium stearate were compressed into microtablets weighing 15.0 mg and having a diameter of 3 mm.

The microtablets were coated at 60° C. inflow air temperature initially with 2 wt. % of an undercoat consisting of Opadry OY 29020 clear, relative to the weight of the tablet cores, and then with 8 wt. % of retard coating, relative to the weight of the tablets plus undercoat. The final weight of the resulting microtablets was 16.6 mg. The resulting delayed release Tramadol microtablets had the following composition:

| | |
|---|---|
| Tramadol hydrochloride | 10.0 mg |
| Microcrystalline cellulose (Avicel PH 101 from FMC) | 4.0 mg |
| Povidon K30 | 0.8 mg |
| Magnesium stearate | 0.2 mg |
| Opadry OY 29020 clear | 0.3 mg |
| Aquacoat ECD 30 (dry substance fraction) | 1.0 mg |
| Dibutyl sebacate | 0.3 mg |
| Total | 16.6 mg |

Diclofenac tablets were produced in a similar manner to the Tramadol microtablets and were likewise compressed into microtablets weighing 15 mg and having a diameter of 3 mm. The microtablets are rendered resistant to gastric juices with an 8 wt. % coating of polyacrylate dispersion. The resulting gastric juice-resistant Diclofenac microtablets had the following composition:

| | |
|---|---|
| Diclofenac-Na | 10.0 mg |
| Microcrystalline cellulose (Avicel PH 101 from FMC) | 4.0 mg |
| Povidon K30 | 0.8 mg |
| Magnesium stearate | 0.2 mg |
| Eudragit L 30 D (dry substance fraction) | 1.0 mg |
| Triethyl citrate | 0.1 mg |
| Talcum | 0.1 mg |
| Total | 16.2 mg |

Ten Tramadol retard microtablets and five Diclofenac microtablets with a gastric-juice resistant coating were packed in hard gelatin capsules of size 0. The release profile was as follows:

|  | Released Fraction in % | |
| --- | --- | --- |
| Time in mins. | for Tramadol | for Diclofenac |
| 120 | 11 | 0 |
| 240 | 37 | 82 |
| 360 | 64 | 96 |
| 480 | 98 | 99 |

The foregoing description and examples have been set forth merely to illustrate the invention and are not intended to be limiting. Since modifications of the described embodiments incorporating the spirit and substance of the invention may occur to persons skilled in the art, the invention should be construed broadly to include all variations falling within the scope of the appended claims and equivalents thereof.

What is claimed is:

1. An oral administration unit comprising a first active substance tramadol or a pharmaceutically acceptable salt thereof, and a second active substance diclofenac or a pharmaceutically acceptable salt thereof, wherein:
    the two active substances are present in separate subunits so as to not impair the release profiles of the two active substances;
    the separate subunits are present in multiparticulate form;
    the active substances tramadol and diclofenac are contained in a quantitative ratio of 1:4 to 4:1; and
    the tramadol and the diclofenac are released in amounts of more than 70% and more than 60% by weight, respectively, within 8 hours.

2. An oral administration unit according to claim 1, wherein the first active substance is a pharmaceutically acceptable salt of tramadol selected from the group consisting of tramadol hydrochloride, tramadol hydrobromide, tramadol sulfate, tramadol phosphate, tramadol fumarate, tramadol succinate, tramadol maleate, tramadol nitrate, tramadol acetate, tramadol propionate, tramadol malonate, tramadol citrate, tramadol tartrate, tramadol benzoate, tramadol salicylate, tramadol phthalate and tramadol nicotinate, and the second active substance is a pharmaceutically acceptable salt of diclofenac selected from the group consisting of diclofenac-sodium, diclofenac-potassium, diclofenac-calcium, diclofenac-magnesium and diclofenac-cholestyramine.

3. An oral administration unit according to claim 2, wherein the pharmacologically acceptable salt of tramadol is tramadol-HCl.

4. An oral administration unit according to claim 2, wherein the pharmacologically acceptable salt of diclofenac is diclofenac-Na.

5. An oral administration unit according to claim 1, wherein the quantitative ratio of tramadol to diclofenac is 1:2 to 3:1.

6. An oral administration unit according to claim 5, wherein the quantitative ratio of tramadol to diclofenac is 1:1 to 2.5:1.

7. An oral administration unit according to claim 1, wherein the subunits are each present in a form independently selected from the group consisting of microtablets, microcapsules, ion-exchange resinates, granules, active substance crystals, and pellets.

8. An oral administration unit according to claim 7, wherein the subunits are each present in the form of pellets or composite pellets produced by extrusion or spheronisation.

9. An oral administration unit according to claim 1, wherein at least one of the two active substances is present in a controlled release formulation.

10. An oral administration unit according to claim 9, wherein both active substances are present in a controlled release formulation.

11. An oral administration unit according to claim 9, wherein the controlled release formulation is effected via coating the at least one active substance, binding the at least one active substance to an ion-exchange resin, embedding the at least one active substance in a controlled release matrix, or a combination thereof.

12. An oral administration unit according to claim 11, wherein the at least one active substance is coated with a coating of a water-insoluble polymer or wax.

13. An oral administration unit according to claim 12, wherein the at least one active substance is coated with a water-insoluble polymer selected from the group consisting of polyacrylate resins and cellulose derivatives.

14. An oral administration unit according to claim 13, wherein the at least one active substance is coated with a water-insoluble alkylcellulose.

15. An oral administration unit according to claim 12, wherein the at least one active substance is coated with a water-insoluble ethylcellulose or poly(meth)acrylate polymer.

16. An oral administration unit according to claim 11, wherein the controlled release formulation is effected by embedding the at least one active substance in a controlled release matrix.

17. An oral administration unit according to claim 9, wherein the oral administration unit further comprises at least one of the active substances in a non-controlled release form.

18. An oral administration unit according to claim 1, wherein the oral administration unit is a sachet, a capsule or a tablet.

19. An oral administration unit according to claim 18, wherein the oral administration unit is a capsule or a pellet tablet.

20. An oral administration unit according to claim 18, wherein the oral administration unit is a rapidly decomposing tablet.

21. An oral administration unit according to claim 20, wherein the oral administration unit is a rapidly decomposing pellet tablet.

22. An oral administration unit according to claim 18, further comprising a release layer that effects a dissociation of the subunits from one another on contact with an aqueous body fluid.

23. An oral administration unit according to claim 18, wherein the oral administration unit is a tablet having a score mark to facilitate subdivision of the tablet.

24. An oral administration unit according to claim 18, wherein the oral administration unit has a gastric juice-resistant coating.

25. An oral administration unit according to claim 18, wherein the oral administration unit is a capsule.

* * * * *